| United States Patent [19] | [11] 4,122,187 |
|---|---|
| Kotani et al. | [45] Oct. 24, 1978 |

[54] SORBIC ACID COMPOSITION HAVING IMPROVED QUALITY

[75] Inventors: Yasuo Kotani, Hirakata; Masayasu Hasegawa, Kyoto, both of Japan

[73] Assignee: Nippon Gohsei Kagaku Kogyo Kabushiki Kaisha, Osaka, Japan

[21] Appl. No.: 838,379

[22] Filed: Sep. 30, 1977

[30] Foreign Application Priority Data

Oct. 5, 1976 [JP] Japan .................................. 51-120538
Jul. 1, 1977 [JP] Japan .................................. 52-79325

[51] Int. Cl.² ........................................................ A01N 9/24
[52] U.S. Cl. ........................................ 424/317; 426/532; 426/335
[58] Field of Search ............... 426/532, 335; 424/314, 424/317

[56] References Cited

U.S. PATENT DOCUMENTS 3,934,045  1/1976  Fernholz et al. .................... 426/335

FOREIGN PATENT DOCUMENTS 6,804,299  9/1968  Netherlands ............................. 426/532

*Primary Examiner*—Raymond N. Jones
*Assistant Examiner*—Elizabeth A. Hatcher
*Attorney, Agent, or Firm*—Armstrong, Nikaido, Marmelstein & Kubovcik

[57] ABSTRACT

A sorbic acid composition having improved quality which comprises (a) sorbic acid or a double salt thereof and (b) 0.05 to 5 parts by weight of glycerin to 100 parts by weight of (a). The incorporation of glycerin restrains the offensive odor and the scattering of the fine powders of sorbic acid and double salts thereof.

3 Claims, No Drawings

SORBIC ACID COMPOSITION HAVING IMPROVED QUALITY

BACKGROUND OF THE INVENTION

The present invention relates to a sorbic acid composition having the improved quality.

Sorbic acid and double salts thereof such as sorbic acid-potassium sorbate double salt are well known as preservatives for foods. Particularly, they are added as antiseptics and antifungal agents to processed meat products such as ham and sausage, dairy products such as butter and cheese, fish-paste products and wine, and exhibit the excellent effect. The sorbic acid and double salts thereof are hereinafter referred to as "sorbic acids".

The sorbic acids are put on the market as fine crystals. When the sorbic acids are employed for the above purpose, the particles being as small as possible are preferred, since a trace amount of the sorbic acids must be uniformly incorporated into foods. However, the powders of the sorbic acids having a particle size of less than 150 $\mu$, particularly of less than 100 $\mu$ are easy to scatter in handling, for instance, upon putting them into a bag or upon adding them to foods. Also, such fine powders have an irritating odor. Thus, the fine powders have a poor workability. Therefore, the commercially available powders are generally those having an average particle size of more than 150 $\mu$, particularly 200 to 300 $\mu$, but fine particles of less than 100 $\mu$ in particle size are included therein though a small amount.

As a means for improving workability of the fine powders of sorbic acids, it has been proposed to mold the fine powders in granular form. However, the thus prepared granules of the sorbic acids are poor in rigidity and inevitably produce the fine powders by the breakdown of a part of the granules during transportation or handling.

It is also proposed to coat the surfaces of the powders of sorbic acid with a hardened oil, as disclosed in Japanese Patent Publication No. 14104/1970. The irritating odor disappears, but the dispersibility into water lowers and the uniform incorporation into foods becomes hard.

OBJECTS OF THE INVENTION

It is an object of the present invention to provide powdery sorbic acids having improved workability.

A further object of the invention is to provide a sorbic acid composition which does not scatter in handling and does not give out an irritating odor.

These and other objects of the invention will become apparent from the description hereinafter.

DETAILED DESCRIPTION

It has now been found that the above-mentioned objects can be attained by blending the sorbic acids with a specific amount of glycerin.

The improvement of the quality of the powdery sorbic acids by the blending with additives has been attempted with respect to polyhydric alcohols such as ethylene glycol and propylene glycol, lactic acid, sucrose, hardened oils and glycerides as well as glycerin. However, the polyhydric alcohols other than glycerin, lactic acid and sucrose have little effect of restraining the irritating odor of the fine powders. Also, the hardened oils and glycerides are required in at least 1.5 times sorbic acids for restraining the irritating odor, and the sorbic acids blended therewith become very poor in dispersibility into water. This results in the lowering of the uniform incorporation into foods and the utility of the sorbic acids are limited.

The sorbic acid composition containing glycerin of the present invention can remarkably decrease the irritating odor and the scattering of the fine powders of sorbic acids and also can be uniformly incorporated into foods with ease. Moreover, the antiseptic effect of the sorbic acids cannot be impaired by the addition of glycerin.

In order to obtain the above-mentioned effects, it is necessary to blend the sorbic acids with at least 0.05 parts by weight of glycerin to 100 parts by weight of the sorbic acids. The effects cannot be obtained by the blending with glycerin in a smaller amount than this. On the other hand, even if glycerin is employed in an amount of more than 5 parts by weight to 100 parts by weight of the sorbic acids, the effects do not increase, but rather decrease in long storage and the powders tend to agglutinate. Therefore, glycerin is employed in an amount of 0.05 to 5 parts by weight, preferably 0.5 to 3 parts by weight to 100 parts by weight of the sorbic acids.

The blending of the sorbic acids with glycerin is conducted by mixing them in a usual manner, and it is suitable to mix them as uniformly as possible. In order to uniformly mix such a small amount of glycerin with the sorbic acids, glycerin is preferably diluted with a solvent such as water, an aqueous solution of an alcohol and acetone, and is mixed with the powders of sorbic acids with agitation and then the mixture is dried. It may also be employed to spray a glycerin solution over the powders of sorbic acids. The solvent is usually employed in an amount of 50 to 100% by weight based on the weight of the sorbic acids. Usual mixers or blenders may be used for mixing the powders and solvent. Also, the drying is advantageously carried out at a low temperature of about 10° to about 40° C. under reduced pressure to avoid the change in quality and the sublimation loss of the sorbic acids.

The sorbic acids intended in the present invention include sorbic acid and double salts thereof. As the double salts, any known double salts, for instance, as disclosed in Japanese Patent No. 603671 are employed. Examples of the double salts are double salts of sorbic acid with sodium or potassium sorbate, double salts of sorbic acid with sodium or potassium salt of an organic acid such as succinic acid, citric acid, tartaric acid, propionic acid or acetic acid, and double salts of sorbic acid with an inorganic acid salt such as sodium phosphate, potassium phosphate or potassium alum. For instance, sorbic acid-potassium sorbate double salt which is an typical example of the double salts is produced by a process in which sorbic acid is dissolved in 90% ethanol with heating, and after adding to the solution an equimolecular amount of potassium sorbate which is industrially prepared by neutralizing sorbic acid with potassium hydroxide, the solution is heated, or a process in which sorbic acid is dissolved in 90% ethanol with heating and is thermally reacted with about 0.5 mole of potassium hydroxide per mole of sorbic acid, and the resulting reaction mixture is then cooled to precipitate crystals.

The double salts have a strong irritating odor and also the particle size of their crystals is generally small and, therefore, the present invention is very useful for these substances.

As stated before, the present invention has the greatest effect on the fine powders. The problems such as the scattering and irritating odor of the powders are noticeable on the powders having a particle size of less than 150 μ, particularly of less than 100 μ. Therefore, the present invention is applied to the fine powders of the sorbic acids with the greatest effect. However, the powders of the sorbic acids having a particle size of more than 150 μ or the granules of the sorbic acids on the market contain the fine particles though a small amount. Since it is impossible to completely exclude such fine particles from the powders or granules, the blending with glycerin has the great effect even on the commercially available sorbic acids in various forms.

The sorbic acid composition of the present invention may contain known additives for the sorbic acids, such as an antioxidant and surface active agent, as occasion demands.

The thus obtained composition can be effectively employed in any fields requiring the prevention of the growth of molds and microorganisms, for instance, may be employed for foods, medicines and cosmetics, or may be utilized as fungicides.

The present invention is more specifically described and explained by means of the following Examples.

EXAMPLES 1 TO 5 AND COMPARATIVE percent transmission was measured by a photoelectric colorimeter (OD: 660 mμ) after 5, 10, 20, 30, 40, 50 and 60 seconds from the addition with continuous mild agitation, and the time until the percent transmission became constant was obtained. This result shows that the shorter the time, the better the dispersibility.

The results are shown in Table 1.

Table 1

| Example No. | Amount of glycerin added g. | Immediately after drying | | After 2 months | |
|---|---|---|---|---|---|
| | | Odor | Dispersibility into water sec. | Odor | Dispersibility into water sec. |
| 1 | 0.1 | 4 | 10 | 4 | 10 |
| 2 | 0.5 | 2 | 5 | 2 | 5 |
| 3 | 1.0 | 2 | 5 | 2 | 5 |
| 4 | 2.0 | 1 | 5 | 2 | 5 |
| 5 | 4.0 | 1 | 5 | 2 | 10 |
| Com. Ex. 1 | 10 | 1 | 5 | 4 | 10 |
| Com. Ex. 2 | 20 | 2 | 5 | 4 | 10 |

COMPARATIVE EXAMPLES 3 TO 15

Experiments were conducted according to Examples 1 to 5.

The results are shown in Table 2.

Table 2

| Comparative Example No. | Additive | Amount of additive g. | Immediately after drying | | After 2 months | |
|---|---|---|---|---|---|---|
| | | | Odor | Dispersibility into water sec. | Odor | Dispersibility into water sec. |
| 3 | — | 0 | 5 | 40 | 5 | 40 |
| 4 | Glycerin | 30 | 3 | 5 | 4 | 30 |
| 5 | Ethylene glycol | 1 | 4 | 5 | 5 | 40 |
| 6 | Ethylene glycol | 4 | 4 | 5 | 5 | 30 |
| 7 | Propylene glycol | 1 | 5 | 5 | 5 | 40 |
| 8 | Propylene glycol | 4 | 4 | 5 | 5 | 40 |
| 9 | Lactic acid | 1 | 4 | 10 | 5 | 40 |
| 10 | Lactic acid | 4 | 4 | 5 | 5 | 30 |
| 11 | Sucrose | 1 | 5 | 10 | 5 | 40 |
| 12 | Sucrose | 4 | 4 | 10 | 5 | 30 |
| 13 | Hardened oil | 1 | 4 | 40 | 5 | 40 |
| 14 | Hardened oil | 4 | 4 | not disperse* | 5 | not disperse* |
| 15 | Hardened oil | 150 | 2 | not disperse* | 4 | not disperse* |

*Composition did not disperse into water due to floating on water surface.

EXAMPLES 1 AND 2

To 100 g. of fine powders of sorbic acid having a particle size ranging from 5 to 30 μ was added 100 g. of an aqueous solution of glycerin containing the prescribed amount of glycerin as shown in Table 1. After mixing with agitation, the resulting mixture was dried at room temperature under reduced pressure. The odor test and the test of dispersibility into water were conducted on the obtained composition in the form of fine powder immediately after drying and after storing at 38° c. for 2 months.

With respect to the odor test, the organoleptic test was conducted on a panel member composed of ten persons. The degree of odor was shown as follows:
5: Very strong odor
4: Strong odor
3: Slight odor
2: Little odor
1: No odor The dispersibility into water was estimated by measuring the time that the composition took for uniformly dispersing into water. The test was conducted as follows: A test tube was charged with 10 ml. of water, and 0.5 g. of the composition was added thereto. Then the

EXAMPLES 6 TO 10 AND COMPARATIVE EXAMPLES 16 AND 17

The procedures of Examples 1 to 5 were repeated except that sorbic acid-potassium sorbate double salt having an average particle size of 100 to 200 mesh was employed instead of sorbic acid.

The results are shown in Table 3.

Table 3

| Example No. | Amount of glycerin added g. | Immediately after drying | | After 2 months | |
|---|---|---|---|---|---|
| | | Odor | Dispersibility into water sec. | Odor | Dispersibility into water sec. |
| 6 | 0.1 | 2 | 10 | 2 | 10 |
| 7 | 0.5 | 1 | 5 | 1 | 5 |
| 8 | 1.0 | 1 | 5 | 1 | 5 |
| 9 | 2.0 | 1 | 5 | 1 | 10 |
| 10 | 5.0 | 1 | 5 | 2 | 10 |
| Com. Ex. 16 | 10 | 1 | 4 | 4 | 10 |
| Com. Ex. 17 | 20 | 2 | 5 | 4 | 10 |

COMPARATIVE EXAMPLES 18 TO 30

Experiments were conducted according to Examples 6 to 10.

The results are shown in Table 4.

Table 4

| Comparative Example No. | Additive | Amount of additive g. | Immediately after drying | | After 2 months | |
|---|---|---|---|---|---|---|
| | | | Odor — | Dispersibility into water sec. | Odor — | Dispersibility into water sec. |
| 18 | — | 0 | 5 | 30 | 5 | 30 |
| 19 | Glycerin | 30 | 2 | 4 | 4 | 20 |
| 20 | Ethylene glycol | 1 | 4 | 5 | 5 | 30 |
| 21 | Ethylene glycol | 4 | 4 | 5 | 5 | 30 |
| 22 | Propylene glycol | 1 | 5 | 5 | 5 | 30 |
| 23 | Propylene glycol | 4 | 4 | 5 | 5 | 30 |
| 24 | Lactic acid | 1 | 4 | 5 | 5 | 30 |
| 25 | Lactic acid | 4 | 4 | 5 | 4 | 30 |
| 26 | Sucrose | 1 | 5 | 5 | 5 | 30 |
| 27 | Sucrose | 4 | 4 | 5 | 4 | 30 |
| 28 | Hardened oil | 1 | 5 | 40 | 5 | 40 |
| 29 | Hardened oil | 4 | 4 | not disperse* | 5 | not disperse* |
| 30 | Hardened oil | 150 | 2 | not disperse* | 4 | not disperse* |

*Composition did not disperse into water due to floating on water surface.

What we claim is:

1. A sorbic acid composition comprising (a) sorbic acid or a double salt thereof and (b) 0.05 to 5 parts by weight of glycerin to 100 parts by weight of said (a).

2. The composition of claim 1, wherein said sorbic acid or double salt thereof has an average particle size of less than 150 $\mu$.

3. The composition of claim 1, wherein said double salt is sorbic acid-potassium sorbate double salt.

* * * * *